United States Patent [19]

Wester et al.

[11] Patent Number: 4,600,516
[45] Date of Patent: Jul. 15, 1986

[54] SULFONATED TRIBUTYLPHENOL ETHOXYLATES, THEIR USE, AND A PROCESS FOR PREPARING SULFONATED ALKOXYLATES

[75] Inventors: Norbert Wester, Hofheim am Taunus; Klaus Uhl, Bad Soden am Taunus; Walter Gulden, Hofheim am Taunus; Gerhart Schneider, Königstein, all of Fed. Rep. of Germany

[73] Assignee: Hoechst Aktiengesellschaft, Frankfurt, Fed. Rep. of Germany

[21] Appl. No.: 580,436

[22] Filed: Feb. 15, 1984

[30] Foreign Application Priority Data

Feb. 17, 1983 [DE] Fed. Rep. of Germany ....... 3305328
Dec. 23, 1983 [DE] Fed. Rep. of Germany ....... 3346676

[51] Int. Cl.⁴ ................... C09K 3/00; C07C 143/42; C07C 143/02
[52] U.S. Cl. ................... 252/8.55 R; 166/274; 166/275; 260/512 R; 260/513 R; 260/513 B
[58] Field of Search .......... 260/513 B, 513 R, 512 R; 252/8.55 D, 8.55 R; 166/274, 275

[56] References Cited

U.S. PATENT DOCUMENTS

| | | | |
|---|---|---|---|
| 2,115,192 | 4/1938 | Bruson | 260/512 R |
| 2,148,432 | 2/1939 | Bruson | 260/512 R |
| 3,082,249 | 3/1963 | Gaertner | 260/513 B |
| 3,275,682 | 9/1966 | Bakker | 260/513 B |
| 3,541,140 | 11/1970 | Murphy | 260/513 B |
| 4,091,014 | 5/1978 | Johnson | 260/512 R |
| 4,343,711 | 8/1982 | Kafoglou | 260/513 B |

*Primary Examiner*—Theodore Morris
*Attorney, Agent, or Firm*—Connolly and Hutz

[57] ABSTRACT

Sulfonated tributylphenol ethoxylates of the formula

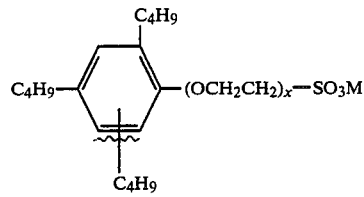

where x denotes a number from 2 to 20, and M denotes a cation, their use as surfactants, in particular as auxiliaries in the tertiary production of crude oil, and an improved, general process for preparing sulfonated alkyl and (alkyl)aryl polyalkoxylates by reacting halides of alkyl and (alkyl)aryl polyethoxylates with alkali metal sulfite by carrying out the reaction in the presence of lower alcohols, polyols, monoethylene glycol, polyethylene glycol or alkyl ethers thereof, as solubilizing agents.

6 Claims, No Drawings

SULFONATED TRIBUTYLPHENOL ETHOXYLATES, THEIR USE, AND A PROCESS FOR PREPARING SULFONATED ALKOXYLATES

Sulfonated alkyl and alkylaryl polyalkoxylates are of great interest because of their high stability to acid and alkali and because of their excellent compatibility with salt. They are highly suitable for cleaning purposes in alkaline and acid media. Owing to their excellent capacity for emulsifying fats and oils, they are also used in, for example, lime soap formulations and in emulsion polymerization processes. They, moreover, are useful as auxiliaries at the assisted stage of crude oil production.

Methods for their preparation have been described, for example in German Pat. No. 2,748,722 and U.S. Pat. Nos. 4,091,014 and 2,535,677. In another method of preparation, alkyl or alkylaryl polyalkoxylates with terminal halogen are reacted in aqueous solution at elevated temperatures with $Na_2SO_3$ under alkaline catalysis (European Patent 26,932) or without catalyst (U.S. Pat. Nos. 2,148,432 and 2,115,192) to give the respective sulfonated alkoxylates. Alkyl sulfonates without alkylene oxide chains can be prepared, for example, by reacting alkyl halides at relatively low temperatures in an appropriate manner in the presence of a quaternary ammonium compound (German Pat. No. 2,545,644).

The problem with replacing halogen by sulfite is that the two reactants, namely halogen-terminated oxyethylate and $Na_2SO_3$, are present in two different phases, separate from each other. The degree of phase separation is considerably increased by the high reaction temperatures required for the reaction, which, in some instances, are far above the cloud points of the ethoxylates used. And, in a side reaction, the halides are increasingly hydrolyzed to the corresponding alcohols, and there is, as a consequence, a considerable drop in the yield of desired sulfonated alkoxylate, in particular in the case of higher-oxyalkylated compounds. Attempts to allow for this fact take the form of, for example, vigorous stirring (European Pat. No. 26,932) or using quaternary ammonium compounds in the case of alkyl sulfonates (German Pat. No. 2,545,644).

It has now been found, surprisingly, that adding certain solubilizing agents to this reaction considerably increases the yields, considerably shortens the length of reaction and, what is more, produces more easily handled products.

The invention provides a process for preparing sulfonated alkoxylates of the formula

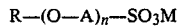

in which R denotes $C_8$–$C_{22}$-alkyl, preferably $C_{12}$–$C_{18}$-alkyl, or phenyl or naphthyl, both of which can be substituted by 1 to 3 $C_1$–$C_{15}$-alkyl, preferably $C_4$–$C_{12}$-alkyl, A preferably denotes an ethylene or an isopropylene group, n denotes a number from 1 to 30, preferably 6 to 20, and M denotes sodium or potassium.

The novel process comprises reacting a compound of the formula

in which Hal denotes a halogen atom, in aqueous solution with sodium sulfite or potassium sulfite in the presence of lower alcohols, polyols, monoethylene glycol, polyethylene glycol or alkyl ethers thereof.

The essence of the invention is thus the addition of specific alcohols as solubilizing agents. Suitable for this purpose are $C_1$–$C_4$-alkanols, polyols, such as, preferably, glycerol, ethylene glycol or polyethylene glycols, in particular diethylene to tetraethylene glycols, and their $C_1$–$C_4$-alkyl monoethers or diethers. All in all, the process is preferably carried out with monoethylene, diethylene or triethylene glycol. The amount of these alcohols in the starting batch for the reaction is about 2 to 60, preferably 10 to 40, % by weight, based on the alkoxylate halide. The reaction is carried out at temperatures of 120° to 200°, preferably at 160° to 180° C. The length of the reaction is only 2 to 10, preferably 3 to 6, hours. The sulfite is used in a slight excess in the form of sodium sulfite or potassium sulfite. The reaction medium used is water, in which, at the start of the reaction, the total concentration of the two starting compounds is preferably about 40%. The reaction can be speeded up by also adding conventional substitution catalysts, such as, for example, alkali metal iodides.

This process produces the sulfonated alkoxylates in a high yield, namely above 80%. The resulting aqueous solutions of the sulfonated alkoxylates can be directly used as they are, i.e. without isolating the sulfonated alkoxylates. By virtue of containing alcohols of the type described above, these solutions are much less likely to form gels.

The invention also provides novel sulfonated tributylphenol ethoxylates of the formula

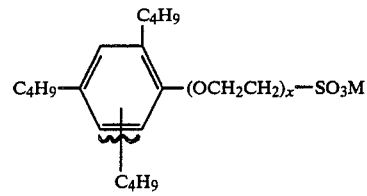

where x denotes a number from 2 to 20, preferably 2 to 12, and M denotes $Na^+$, $K^+$, $NH_4^+$ or the cation of an amine base. These compounds can likewise be prepared with the process described above.

The compounds of the above formula are derived from tributylphenol, preferably from technically accessible mixtures of 2,4,6-isotributylphenol and a minor 2,4,5-isotributylphenol content, this mixture also containing small amounts of isodibutylphenol and isotetrabutylphenol. An example thereof is a mixture comprising 1.4–2% of 2,6-isodibutylphenol, 0.3–0.8% of 2,4-isodibutylphenol, 1.2–2.2% of 2,5-isodibutylphenol, 70–80% of 2,4,6-isotributylphenol, 9–12% of 2,4,5-isotributylphenol and 6–7% of 2,4,5,6-isotetrabutylphenol, the total proportion of the three isodibutyl isomers amounting to about 3%.

Sulfonated alkoxylates, including in particular the sulfonated tributylphenol ethoxylate of the above formula are surfactants which are distinguished by their stability over a wide temperature and pH range. Aqueous solutions of these compounds reduce the surface tension at the surfactant solution/air phase boundary to values of the order of 25 to 30 $mNm^{-1}$ and the oil/surfactant solution interfacial tension to values of $10^{-2}$ to $10^{-4}$ $mNm^{-1}$ (after Di Nouy). Owing to their effectiveness and stability over a wide pH range, these compounds are suitable for alkaline and for acid metal-cleaning processes. They are also effective emulsifying agents for emulsion polymerization processes and are suitable for use as stabilizers for latex and other polymer emulsions. These compounds are also of particular interest for use in the production of crude oil, such as, for example, in the stimulation of wells and the fracturing of crude oil deposits. This involves making the environment of a production well more permeable to the oil by treatment with acid or by breaking up (fracturing) the deposit by applying very high pressure. The use of the compound according to the present invention increases the oil yield in these processes. In all cases the surfactant is generally used in amounts of 0.01 to 10, preferably 0.05 to 3, %.

EXAMPLE 1

Sulfonated condensation product of tributylphenol and 7.5 moles of ethylene oxide 452 g (0.75 mole) of the chloride prepared by reacting the condensation product of tributylphenol and 7.5 moles of ethylene oxide (OH number: 96) with $SOCl_2$ are introduced into a 2 liter pressure autoclave together with 104 g (0.825 mole) of $Na_2SO_3$, a spatula tip of NaI, 83 g of diethylene glycol and 751 g of water, and the mixture, which has a starting pH of 10–11, is stirred at 175° C. for 3 hours. It is allowed to cool down to about 50° C. and is racked. The reaction product is an orange viscous clear substance with a 30.4% content (which corresponds to 84% of the theoretical amount of sulfonate based on a molecular weight of 670).

EXAMPLE 2

Sulfonated condensation product of tributylphenol and 7.5 moles of ethylene oxide Example 1 was repeated, except that triethylene glycol was used as solubilizing agent in place of diethylene glycol. Content: 30.1% (83.2% of theory).

EXAMPLE 3

Sulfonated condensation product of tributylphenol and 10 moles of ethylene oxide 385 g (0.5 mole) of the chlorine compound prepared by reacting the condensation product of tributylphenol and 10 moles of ethylene oxide (OH number: 75) with $SOCl_2$ are introduced into a 2 liter pressure autoclave together with 69.3 g (0.55 mole) of $Na_2SO_3$, a spatula tip of NaI, 69 g of diethylene glycol and 618 g of water, and the mixture, which has a starting pH of 10–11, is stirred at an internal temperature of 175° C. for 5 hours. When the reaction is complete, the mixture is allowed to cool down to about 50° C. and is racked. The reaction product is a yellow, viscous, clear liquid having a 29.0% content (80.4% of theory based on a molecular weight of 824).

EXAMPLE 4

Sulfonated condensation product of tributylphenol and 10 moles of ethylene oxide Same starting batch as in Example 3, except that triethylene glycol is used as the solubilizing agent. Content: 29.6% (82% of theory).

EXAMPLE 5

Sulfonated condensation product of tributylphenol and 13 moles of ethylene oxide 440 g (0.5 mole) of the chloride prepared by reacting the condensation product of tributylphenol and 13 moles of ethylene oxide (OH number: 65) with $SOCl_2$ are introduced into a 2 liter stirred autoclave together with 69.3 g (0.55 mole) of $Na_2SO_3$, a spatula tip of NaI, 75 g of diethylene glycol and 690 g of water, and the mixture, which has a starting pH of 10–11, is stirred at an internal temperature of 175° C. for 5 hours. This gives a brown, viscous liquid with a 29.9% content (80.2% of theory based on a molecular weight of 949).

EXAMPLE 6

Sulfonated condensation product of Alfol 14 and 3 moles of ethylene oxide (Alfol 14=$C_{14}$-alcohol)

350 g (0.94 mole) of the chloride prepared by reacting the condensation product of Alfol 14 and 3 moles of ethylene oxide (OH number: 159) with thionyl chloride are introduced into a 2 liter pressure autoclave together with 130.6 g (1.04 moles) of $Na_2SO_3$, a spatula tip of NaI, 72 g of diethylene glycol and 650 g of water, and the mixture, which has a starting pH of 10–11, is stirred at 175° C. for 6 hours. It is allowed to cool down to 60° C. and is racked. The end product has a 31.4% content (91.3% of theory based on a molecular weight of 439).

EXAMPLES 7–9

The following were prepared in corresponding manner:

sulfonated condensation product of tallow-fat alcohol and 8 moles of ethylene oxide (80.1% of theory), sulfonated condensation product of isotridecyl alcohol and 6 moles of ethylene oxide (85.4% of theory) and sulfonated condensation product of isotridecyl alcohol and 8 moles of ethylene oxide (80.3% of theory).

COMPARATIVE EXAMPLE 1

(analogous to Example 6 of European Pat. No. 26,932)

Sulfonated condensation product of tributylphenol and 10 moles of ethylene oxide 385 g (0.5 mole) of the chloride prepared by reacting the condensation product of tributylphenol and 10 moles of ethylene oxide (OH number: 75) with $SOCl_2$, 69.3 g (0.55 mole) of $Na_2SO_3$, 3 g of 50% strength sodium hydroxide solution and 680 g of water are stirred at 160°–165° C. in a 1 liter pressure autoclave for 20 hours. When the reaction is complete the mixture is allowed to cool down to 40° C. and is racked. This gives a highly viscous, yellow product having a 26.1% content (72.1% of theory based on a molecular weight of 824).

COMPARATIVE EXAMPLE 2

(analogous to Example 1 of German Pat. No. 2,545,644)

Sulfonated condensation product of tributylphenol and 10 moles of ethylene oxide 385 g (0.5 mole) of the chlorine compound prepared by reacting the condensation product of tributylphenol and 10 moles of ethylene oxide (OH number: 75) with thionyl chloride, 74.3 g (0.59 mole) of $Na_2SO_3$, 4.3 g (0.013 mole) of tetrabutylammonium hydrogensulfate, 200 ml of ethanol and 500 ml of water are refluxed at 90°

C. for 20 hours. The sulfonate content of the product obtained on distilling off the solvent was 2%, and its organically bonded chlorine content was 4.7% (=that of the starting compound).

COMPARATIVE EXAMPLE 3

(analogous to Example 1 of German Pat. No. 2,545,644, with upper preferred amount of quaternary ammonium compound)

77 g (0.1 mole) of the chloride prepared by reacting the condensation product of tributylphenol and 10 moles of ethylene oxide (OH number: 75) with $SOCl_2$ are refluxed at 90° C. for 20 hours together with 12.6 g (0.1 mole) of $Na_2SO_3$, 4.7 g (0.014 mole) of tetrabutylammonium hydrogensulfate, 200 ml of ethanol and 500 ml of water. The product obtained on evaporating the solvent had a 2% content.

The significantly poorer results of the comparative examples underline the outstanding suitability of the novel process claimed here for preparing sulfonated alkoxylates.

To determine the effectiveness of sulfonated tributylphenol ethoxylates, use is made of the microcapillary deoiling method described in U.S. Pat. No. 4,008,165 and the determination of interfacial tension by the spinning drop interfacial tensiometer method.

In the microcapillary deoiling method, glass microcapillaries made by Drummond Scientific Co. (USA) and having a volume of 5 µl, a length of 30 mm and a diameter of 0.45 mm are used as a model of the pore space of the geological deposit.

The microcapillaries are sealed at one end by melting, are evacuated in a desiccator, and are filled with crude oil. The capillaries are introduced in a vertical position, with the opening at the top, into surfactant solutions (test tubes) which are being temperature-conditioned in a waterbath, and the displacement of the oil is visually recorded as a function of time.

The effectiveness of the surfactants can be determined by means of the following assessment scheme as a function of the surfactant concentration, the salt concentration, the pH, the temperature and the composition of the oil.

| Value | |
|---|---|
| 9 | empty (30 mm) after 10 minutes |
| 8 | empty after 1 hour |
| 7 | empty after 3 hours |
| 6 | empty after 20 hours |
| 5 | 16-25 mm emptied after 20 hours |
| 4 | 9-15 mm emptied after 20 hours |
| 3 | 4-8 mm emptied after 20 hours |
| 2 | 1-3 mm emptied after 20 hours |
| 1 | a trace emptied after 20 hours |
| 0 | unchanged after 20 hours |

This method offers the advantage that, since the microcapillaries have a narrow diameter, the viscosity and density of the oils have no great effect on the deoiling action, and that it is possible to work with deposit oil and deposit water.

According to Taber in J. Petr. Techn. 3 (1969), pages 3–12, surfactants are suitable for tertiary production of crude oil only when the interfacial tension at the oil/salt water phase boundary is reduced to values less than $10^{-2}$ $mNm^{-1}$. This determination of the interfacial tension at the oil/water phase boundary is done by means of the spinning drop interfacial tensiometer developed by Wade and Burkowsky (M. Burkowsky and C. Marx: On the mechanism of surfactant-flooding in highly saline systems; Erdöl-Erdgas-Zeitschrift 95 (1979), pages 17–25).

The method is based on the fact that an oil drop introduced into a capillary which rotates about its horizontal axis and which contains a liquid (salt water+surfactant) of higher density is deformed. The drop is stretched until the deforming forces and the interfacial tension are in equilibrium.

According to Vonnegut (B. Vonnegut, Rev. Sci. Instruments 13 (1942), pages 6–9), the interfacial tension can be calculated from the measured oil drop diameter R, the speed of rotation W and the density difference Δd by the following formula:

$$\gamma^{1/2} = \frac{\Delta d \cdot W^2 \cdot R^3}{4}$$

The values measured with these methods are given in the tables below. In all cases a 1% strength aqueous solution of each surfactant was used. For the purposes of comparison with the state of the art, sulfonated nonylphenol and dinonylphenol ethoxylates were also tested.

I. TEST WITH DEPOSIT OIL K

Salt content per liter: 180 g of NaCl, 20 g of $CaCl_2$; pH 8.5; temperature: 40° C.

| | Interfacial tension ($mNm^{-1}$) | Microcapillary deoiling |
|---|---|---|
| 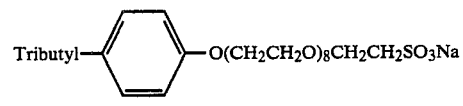 Tributyl—⟨phenyl⟩—$O(CH_2CH_2O)_8CH_2CH_2SO_3Na$ | $2 \times 10^{-3}$ | 6 |
| 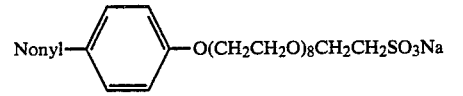 Nonyl—⟨phenyl⟩—$O(CH_2CH_2O)_8CH_2CH_2SO_3Na$ | $3 \times 10^{-2}$ | 0 |

| | Interfacial tension (mNm$^{-1}$) | Microcapillary deoiling |
|---|---|---|
| Di-Nonyl—C$_6$H$_4$—O(CH$_2$CH$_2$O)$_6$CH$_2$CH$_2$SO$_3$Na | $8 \times 10^{-2}$ | 0 |

II. TEST WITH DEPOSIT OIL K

Salt content per liter: 100 g of NaCl; pH 8.5; temperature: 40° C.

| | Interfacial tension (mNm$^{-1}$) |
|---|---|
| Tributyl—C$_6$H$_4$—O(CH$_2$CH$_2$O)$_4$CH$_2$CH$_2$SO$_3$Na | $1 \times 10^{-2}$ |
| Di-Nonyl—C$_6$H$_4$—O(CH$_2$CH$_2$O)$_6$CH$_2$CH$_2$SO$_3$Na | $8 \times 10^{-2}$ |

III. TEST WITH A PARAFFINIC OIL

Salt content per liter: 135 g of NaCl, 15 g of CaCl$_2$; pH 8.5; temperature: 60° C.

| | Interfacial tension (mNm$^{-1}$) | Microcapillary deoiling |
|---|---|---|
| Tributyl—C$_6$H$_4$—O(CH$_2$CH$_2$O)$_6$CH$_2$CH$_2$SO$_3$Na | $1 \times 10^{-3}$ | 8 |
| Nonyl—C$_6$H$_4$—O(CH$_2$CH$_2$O)$_6$CH$_2$CH$_2$SO$_3$Na | $3 \times 10^{-2}$ | 0 |
| Nonyl—C$_6$H$_4$—O(CH$_2$CH$_2$O)$_6$CH$_2$CH$_2$CH$_2$SO$_3$Na | $8 \times 10^{-2}$ | 0 |
| Di-Nonyl—C$_6$H$_4$—O(CH$_2$CH$_2$O)$_6$CH$_2$CH$_2$SO$_3$Na | $4 \times 10^{-2}$ | 0 |

IV. TEST WITH AN AROMATIC OIL

Salt content per liter: 70 g of NaCl, 30 g of CaCl$_2$; pH 6.5; temperature: 80° C.

| | Interfacial tension (mNm$^{-1}$) |
|---|---|
| Tributyl—C$_6$H$_4$—O(CH$_2$CH$_2$O)$_8$CH$_2$CH$_2$SO$_3$Na | $1.3 \times 10^{-2}$ |
| Nonyl—C$_6$H$_4$—O(CH$_2$CH$_2$O)$_8$CH$_2$CH$_2$SO$_3$Na | $3.8 \times 10^{-2}$ |
| Di-Nonyl—C$_6$H$_4$—O(CH$_2$CH$_2$O)$_8$CH$_2$CH$_2$SO$_3$Na | $8 \times 10^{-2}$ |

V. TEST WITH AN AROMATIC OIL

Salt content per liter: 135 g of NaCl, 15 g of CaCl$_2$; pH 8.5; temperature: 40° C.

| | Interfacial tension (mNm$^{-1}$) | Microcapillary deoiling |
|---|---|---|
| Tributyl—C$_6$H$_4$—O(CH$_2$CH$_2$O)$_6$CH$_2$CH$_2$SO$_3$Na | $3 \times 10^{-3}$ | 8 |

| | Interfacial tension (mNm$^{-1}$) | Microcapillary deoiling |
|---|---|---|
| Nonyl—⬡—O(CH$_2$CH$_2$O)$_6$CH$_2$CH$_2$SO$_3$Na | 1 × 10$^{-2}$ | 0 |
| Nonyl—⬡—O(CH$_2$CH$_2$O)$_6$CH$_2$CH$_2$CH$_2$SO$_3$K | 1 × 10$^{-1}$ | 0 |
| Di-Nonyl—⬡—O(CH$_2$CH$_2$O)$_6$CH$_2$CH$_2$SO$_3$Na | 8 × 10$^{-2}$ | 0 |

VI. TEST WITH AN AROMATIC OIL

Salt content per liter: 105 g of NaCl, 45 g of CaCl$_2$; pH 8.5; temperature: 40° C.

| | Interfacial tension (mNm$^{-1}$) | Microcapillary deoiling |
|---|---|---|
| Tributyl—⬡—O(CH$_2$CH$_2$O)$_6$CH$_2$CH$_2$SO$_3$Na | 2 × 10$^{-3}$ | 8 |
| Nonyl—⬡—O(CH$_2$CH$_2$O)$_6$CH$_2$CH$_2$SO$_3$Na | 1 × 10$^{-2}$ | 0 |
| Nonyl—⬡—O(CH$_2$CH$_2$O)$_6$CH$_2$CH$_2$CH$_2$SO$_3$K | 8 × 10$^{-2}$ | 0 |
| Di-Nonyl—⬡—O(CH$_2$CH$_2$O)$_6$CH$_2$CH$_2$SO$_3$Na | 7 × 10$^{-2}$ | 0 |

VII. TEST WITH A NAPHTHENIC OIL

Salt content per liter: 135 g of NaCl, 15 g of CaCl$_2$; pH 8.5; temperature: 60° C.

| | Interfacial tension (mNm$^{-1}$) | Microcapillary deoiling |
|---|---|---|
| Tributyl—⬡—O(CH$_2$CH$_2$O)$_6$CH$_2$CH$_2$SO$_3$Na | 9 × 10$^{-4}$ | 8 |
| Nonyl—⬡—O(CH$_2$CH$_2$O)$_6$CH$_2$CH$_2$SO$_3$Na | 3 × 10$^{-2}$ | 0 |
| Nonyl—⬡—O(CH$_2$CH$_2$O)$_6$CH$_2$CH$_2$CH$_2$SO$_3$Na | 1 × 10$^{-1}$ | 0 |

|  | Interfacial tension ($mNm^{-1}$) | Microcapillary deoiling |
|---|---|---|
| 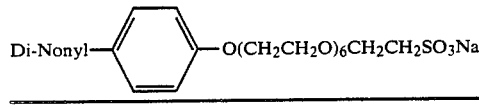 Di-Nonyl—⌬—$O(CH_2CH_2O)_6CH_2CH_2SO_3Na$ | $9 \times 10^{-2}$ | 0 |

VIII. TEST WITH A NAPHTHENIC OIL

Salt content per liter: 140 g of $NaCl_2$, 60 g of $CaCl_2$; pH 6.5; temperature: 60° C.

|  | Interfacial tension ($mNm^{-1}$) | Microcapillary deoiling |
|---|---|---|
| Tributyl—⌬—$O(CH_2CH_2O)_8CH_2CH_2SO_3Na$ | $2 \times 10^{-3}$ | 8 |
| Nonyl—⌬—$O(CH_2CH_2O)_8CH_2CH_2SO_3Na$ | $3 \times 10^{-2}$ | 0 |
| Di-Nonyl—⌬—$O(CH_2CH_2O)_6CH_2CH_2SO_3Na$ | $6 \times 10^{-2}$ | 0 |

IX. TEST WITH A PARAFFINIC (1), NAPHTHENIC (2) AND AROMATIC OIL (3)

Salt content per liter in each case: 150 g of NaCl; pH 6.5; temperature: 80° C.

|  | Interfacial tension ($mNm^{-1}$) | | |
|---|---|---|---|
|  | (1) | (2) | (3) |
| Tributyl—⌬—$O(CH_2CH_2O)_8CH_2CH_2SO_3Na$ | $1.3 \times 10^{-2}$ | $4.2 \times 10^{-3}$ | $1.9 \times 10^{-3}$ |
| Nonyl—⌬—$O(CH_2CH_2O)_8CH_2CH_2SO_3Na$ | $9.4 \times 10^{-2}$ | $3.5 \times 10^{-2}$ | $3.8 \times 10^{-2}$ |
| Di-Nonyl—⌬—$O(CH_2CH_2O)_8CH_2CH_2SO_3Na$ | — | — | $8 \times 10^{-2}$ |

The tables show that the sulfonated isotributylphenol ethoxylates are superior in terms of the degree of oil mobilization to the already known compounds at various salt contents (50-200 g/liter).

These ether sulfonates can also be used in combinations with other anionic surfactants, such as, for example, petroleumsulfonates, secondary-alkanesulfonates, α-olefinsulfonates or dodecylbenzenesulfonates, and nonionic surfactants, such as alkyl or alkylphenol polyglycol ethers. Alcohols and glycol ethers are possible for use as further additives. The viscosity of the flooding water can moreover be increased by means of polymers, such as, for example, hydroxyethylcellulose, polyacrylamides or polysaccharides.

What is claimed is:

1. A process for preparing sulfonated alkoxylates of the formula $$R-(O-A)_n-SO_3M$$

in which R denotes $C_8$-$C_{22}$-alkyl or phenyl or naphthyl, both of which can be substituted by 1 to 3 $C_1$-$C_{15}$-alkyl, A denotes an ethylene or an isopropylene group, n denotes a number from 3 to 30 and M denotes sodium or potassium, which comprises reacting a compound of the formula $$R-(O-A)_n-Hal$$

in which Hal denotes a halogen atom, in aqueous solution with sodium sulfite or potassium sulfite in the presence of monoethylene, diethylene or triethylene glycol.

2. The process as claimed in claim 1, wherein the sulfonated alkoxylates prepared have the formula R—(O—A)$_n$—SO$_3$M in which R is $C_{12}$–$C_{18}$-alkyl or phenyl or naphthyl, both of which can be substituted by 1 to 3 $C_4$–$C_{12}$-alkyl, A denotes an ethylene group, n denotes a number from 6 to 20, and M denotes sodium or potassium.

3. The process as claimed in claim 1, wherein the reaction is carried out at a starting pH of 10–11 in the presence of substitution catalysis, such as NaI or KI.

4. A sulfonated tributylphenol ethoxylate of the formula

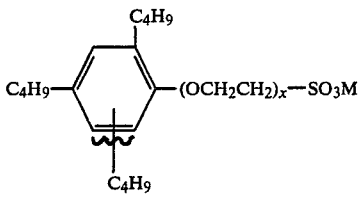

where x denotes a number from 2 to 20, and M denotes Na+, K+, NH$_4$+ or the cation of an amine base.

5. A sulfonated tributylphenol ethoxylate as claimed in claim 4, wherein x is a number from 6 to 20.

6. A method for increasing oil yield in the tertiary production of crude oil by stimulating the oil well and fracturing the crude oil deposits with a composition comprising a compound according to claim 4.

* * * * *